United States Patent

Ishii et al.

Patent Number: 4,985,453
Date of Patent: Jan. 15, 1991

[54] PARABANIC ACID DERIVATIVES AND PHARMACEUTICAL COMPOSITIONS THEREOF

[75] Inventors: Akira Ishii; Masahiro Yamakawa; Yoshio Toyomaki, all of Hyogo, Japan

[73] Assignee: Nippon Zoki Pharmaceutical Co., Ltd., Osaka, Japan

[21] Appl. No.: 385,123

[22] Filed: Jul. 26, 1989

[30] Foreign Application Priority Data

Jul. 29, 1988 [JP] Japan .................................. 63-190921

[51] Int. Cl.$^5$ .................... A61K 31/415; C07D 233/96
[52] U.S. Cl. ....................................... 514/386; 548/307
[58] Field of Search ......................... 548/307; 514/386

[56] References Cited

U.S. PATENT DOCUMENTS 3,766,202 10/1973 Singer .................................. 548/307

FOREIGN PATENT DOCUMENTS 219483 3/1985 German Democratic Rep. ..................................... 548/307
807678 1/1959 United Kingdom ................ 548/307

OTHER PUBLICATIONS

Thornber, C., Chem. Soc. Rev., 1979, 8(4), 563–580.

Primary Examiner—Mary C. Lee
Assistant Examiner—Joseph K. McKane
Attorney, Agent, or Firm—Armstrong, Nikaido, Marmelstein, Kubovcik & Murray

[57] ABSTRACT

Parabanic acid compound of the formula (I):

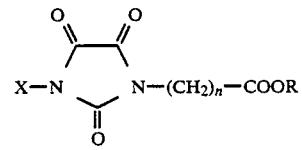

wherein R is hydrogen or a lower alkyl group, X is hydrogen, an alkyl group, a cycloalkyl group, a lower alkylcycloalkyl group, a phenyl group or a phenalkyl group, and n represents an integer of 1 to 4, exhibit excellent aldose reductase inhibitory activity and are useful as drugs for treating or prevention of complications of diabetes.

13 Claims, No Drawings

PARABANIC ACID DERIVATIVES AND PHARMACEUTICAL COMPOSITIONS THEREOF

BACKGROUND OF THE INVENTION

The present invention relates to novel parabanic acid derivatives and pharmaceutically acceptable salts thereof and pharmaceutical compositions containing them as an active ingredient.

Diabetic neuropathy, diabetic cataract and diabetic microangiopathy such as diabetic retinopathy, diabetic nephropathy or diabetic dermopathy are known as intractable chronic diseases accompanied with diabetes. One of the causes of these diabetic complications is the participation of polyol metabolism. Namely, under non-physiological conditions of hyperglycemia in diabetes, the utilization of glucose through polyol pathway increases by several times as high as normal conditions, and so the production of sorbitol is elevated by aldose reductase. Consequently, excessive accumulation of intracellular sorbitol is occurred in tissues such as peripheral nerve, retina, kidney, lens and artery. Under these conditions, cellular edema and functional disorders may be caused by abnormal intracellular osmotic pressure.

As a result of investigations for inhibitors against aldose reductase participating the production of sorbitol to develop new drugs for treatment and prevention of the said diabetic complications, the inventors have found novel parabanic acid derivatives having an excellent aldose reductase inhibitory activity.

An object of the present invention is to provide novel parabanic acid derivatives and pharmaceutically acceptable salts thereof having an excellent aldose reductase inhibitory activity. Another object of the invention is to provide pharmaceutical compositions containing these parabanic acid derivatives or pharmaceutically acceptable salts thereof as an active ingredient to treat diabetic complications.

DETAILED DESCRIPTION OF THE INVENTION

The parabanic acid derivatives of the present invention are represented by the following formula (I):

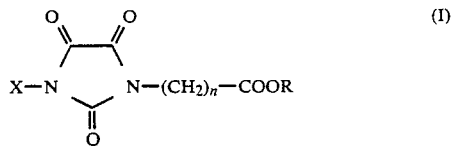

wherein R is hydrogen or a lower alkyl group, X is hydrogen, an alkyl group, a cycloalkyl group, a lower alkylcycloalkyl group, phenyl group or a phenylalkyl group which may optionally have a lower alkyl group, a lower alkoxy group, nitro group or halogen, and n represents an integer of 1 to 4.

In the formula (I), R represents hydrogen or a straight or branched alkyl group having 1 to 4 carbon atoms, such as methyl, ethyl, propyl, isopropyl, butyl, isobutyl, sec-butyl or tert-butyl.

X represents hydrogen; a straight or branched alkyl group having 1 to 8 carbon atoms such as methyl, ethyl, propyl, isopropyl, butyl, isobutyl, sec-butyl, tert-butyl, pentyl, isopentyl, neopentyl, tert-pentyl, hexyl, heptyl or octyl; a cycloalkyl group having 3 to 8 carbon atoms such as cyclopropyl, cyclobutyl, cyclopentyl, cyclohexyl, cycloheptyl or cyclooctyl; a lower alkylcycloalkyl group such as the said cycloalkyl group having a straight or branched alkyl group having 1 to 3 carbon atoms such as methyl, ethyl, propyl or isopropyl; phenyl group; or a phenylalkyl group, for example, an alkyl group of 1 to 6 carbon atoms bonded to phenyl group, such as benzyl, phenylethyl, phenylpropyl, phenylbutyl, phenylpentyl or phenylhexyl, which may optionally have a straight or branched alkyl group having 1 to 3 carbon atoms such as methyl, ethyl, propyl or isopropyl, a straight or branched alkoxy group having 1 to 3 carbon atoms such as methoxy, ethoxy, propoxy or isopropoxy, nitro group or halogen such as fluoride, chloride, bromide or iodide.

The parabanic acid derivatives of the present invention include pharmaceutically acceptable salts of the compounds having formula (I) above, for example, salts as acid addition with an acid such as hydrochloric acid, sulfuric acid, nitric acid, hydrobromic acid, phosphoric acid, perchloric acid, thiocyanic acid, boric acid, formic acid, acetic acid, haloacetic acid, propionic acid, glycolic acid, citric acid, tartaric acid, succinic acid, glyconic acid, lactic acid, malonic acid, fumaric acid, anthranilic acid, benzoic acid, cinnamic acid, p-toluenesulfonic acid, naphthalenesulfonic acid or sulfanilic acid, salts with alkali metal such as sodium or potassium, salts with alkaline-earth metal such as calcium, magnesium or barium, or salts with other metals such as aluminum.

The parabanic acid derivatives of this invention may also include their metal complexes, for example, complexes with zinc, nickel, cobalt, copper, iron etc.

These salts and metal complexes can be produced from free parabanic acid derivatives in the usual way or can be interchanged with each other.

When optical isomers exist in the compounds of the invention, the present invention includes any of the d-, l- and dl-isomers.

The parabanic acid derivatives of the present invention can be prepared as follows:

(i) In an appropriate solvent which does not inhibit the reaction, oxalyl chloride and an N-substituted urea having a substituent corresponding to X in the above formula (I) are stirred at low temperature under ice cooling or at room temperature, or oxalic diester and the said N-substituted urea are stirred at room temperature or at a suitable temperature above room temperature by heating in the presence of an base such as an amine or an alkali metal alkoxide.

Subsequently, in an appropriate solvent which does not inhibit the reaction such as ethanol, the compound obtained by the above method and halogenocarboxylic acid alkyl ester such as methyl bromoacetate, ethyl bromoacetate, ethyl chloroacetate or ethyl bromobutylate were refluxed, if desired with heating, in the presence of a base such as potassium hydroxide to give the compound of the present invention represented by the formula (I) wherein R is a lower alkyl group.

Furthermore, the resulting alkyl ester compound of this invention is hydrolyzed with an acid, for example, the compound is dissolved in a mixture of acetic acid and concentrated hydrochloric acid and refluxed with heating, to give the compound of the present invention represented by the formula (I) wherein R is hydrogen. This compound having hydrogen as R can also produced in a similar manner as mentioned above by using halogenocarboxylic acid instead of halogenocarboxylic acid alkyl ester, not via the said alkyl ester compound.

(ii) Oxalyl chloride and N,N'-disubstituted urea which are substituted with both groups corresponding to X and —(CH$_2$)$_n$—COOR in the formula (I) are stirred at low temperature under cooling or at room temperature in an appropriate solvent which does not inhibit the reaction such as tetrahydrofuran, or the said N,N'-disubstituted urea and oxalic diester are stirred at room temperature or with heating in the presence of an amine or alkali metal alkoxide to give the compound of the present invention.

(iii) After the compound of the present invention represented by the formula (I) wherein X is hydrogen is prepared as mentioned above, the compound is reacted with a halogenated compound of X such as a halogenated alkyl or halogenated benzyl to give the parabanic acid derivative of this invention.

The resulting compounds of the present invention can be purified by known methods such as distillation chromatography and recrystallization. Identification is established through, inter alia, elemental analysis, melting point, IR, NMR, mass spectrum, etc.

EXAMPLES

The following examples, which are illustrative only and not intended to limit the scope of the invention, describe the preparation of the compounds of the present invention.

EXAMPLE 1

2.7 g of potassium hydroxide was dissolved in 150 ml of ethanol. 5.1 g of 1-methylparabanic acid and 10 ml of ethyl bromoacetate were added thereto and the solution was heated under reflux for 6 hours. After cooling, the insoluble substance was filtered off and ethanol was distilled away. The residue was dissolved in ethyl acetate, washed with 5% sodium carbonate and brine, dried over anhydrous sodium sulfate, and passes through silica gel column. Ethyl acetate was distilled away and the residue was recrystallized from hexane to give 3.1 g of ethyl 1-methyl-2,4,5-trioxoimidazolidine-3-acetate (Compound 1).
m.p.: 97°–98.5° C.
Elementary Analysis: C$_8$H$_{10}$N$_2$O$_5$

|  | C % | H % | N % |
| --- | --- | --- | --- |
| Calculated | 44.86 | 4.71 | 13.08 |
| Found | 44.87 | 4.82 | 12.96 |

MS (EI, 70 eV): 214 (M+) 142, 113, 56, 29.
IR (KBr): 2980, 2950, 1725, 1450, 1430, 1215, 1140.
NMR(DMSO-d$_6$/TMS): δ=1.21(t,3H,J=7.1 Hz), 3.03(s,3H), 4.17(q,2H,J=7.1 Hz), 4.39(s,2H).

In the same manner, the following compounds were obtained.
Ethyl 1-butyl-2,4,5-trioxoimidazolidine-3-acetate (Compound 2)
m.p.: 66°–67° C.
Elementary Analysis: C$_{11}$H$_{16}$N$_2$O$_5$

|  | C % | H % | N % |
| --- | --- | --- | --- |
| Calculated | 51.56 | 6.29 | 10.93 |
| Found | 51.29 | 6.51 | 10.65 |

MS (EI, 70 eV): 256 (M+), 201, 184, 183, 182, 155, 140, 127, 100, 70, 56, 41, 29.

IR (KBr): 2950, 2860, 1745, 1720, 1445, 1425, 1405, 1220, 1130.
NMR(DMSO-d$_6$/TMS): δ=0.88(t,3H,J=7.1 Hz), 1.22(t,3H,J=7.1 Hz), 1.29(sex,2H,J=7.1 Hz), 1.56(quin,2H,J=7.1 Hz), 3.54(t,2H,J=7.1 Hz), 4.17(q,2H,J=7.1 Hz), 4.38(s,2H).
Ethyl 1-isobutyl-2,4,5-trioxoimidazolidine-3-acetate (Compound 3)
m.p.: 116°–117° C.
Elementary Analysis: C$_{11}$H$_{16}$N$_2$O$_5$

|  | C % | H % | N % |
| --- | --- | --- | --- |
| Calculated | 51.56 | 6.29 | 10.93 |
| Found | 51.48 | 6.45 | 10.74 |

MS (EI, 70 eV): 256 (M+), 201, 183, 155, 140, 127, 102, 70, 56, 43, 41, 29.
IR (KBr): 2960, 2870, 1745, 1720, 1445, 1430, 1410, 1220, 1135.
NMR(DMSO-d$_6$/TMS): δ=0.88(t,6H,J=7.1 Hz), 1.21(t,3H,J=7.1 Hz), 1.95(m,1H), 3,36(d,2H,J=7.1 Hz), 4.16(q,2H,J=7.1 Hz), 4.40(s,2H).
Ethyl 1-hexyl-2,4,5-trioxoimidazolidine-3-acetate (Compound 4)
Ethyl 1-(4-methylcyclohexyl)-2,4,5-trioxoimidazolidine-3-acetate (Compound 5)
m.p.: 114°–115° C.
Elementary Analysis: C$_{14}$H$_{20}$N$_2$O$_5$

|  | C % | H % | N % |
| --- | --- | --- | --- |
| Calculated | 56.75 | 6.80 | 9.45 |
| Found | 56.68 | 6.83 | 9.69 |

MS (EI, 70 eV): 296 (M+), 223, 201, 155, 127, 96, 81, 67, 55, 41, 29.
IR (KBr): 2950, 2920, 2860, 1750, 1720, 1440, 1125.
NMR(DMSO-d$_6$/TMS): δ=0.88(d,3H,J=6.5 Hz), 1.03(m,2H), 1.22(t,3H,J=7.2 Hz), 1.36(m,1H), 1.73(m,4H), 1.97(m,2H), 3.88(m,1H), 4.17(q,2H,J=7.2 Hz), 4.36(s,2H).
Ethyl 1-benzyl-2,4,5-trioxoimidazolidine-3-acetate (Compound 6)
m.p.: 150°–151° C.
Elementary Analysis: C$_{14}$H$_{14}$N$_2$O$_5$

|  | C % | H % | N % |
| --- | --- | --- | --- |
| Calculated | 57.93 | 4.86 | 9.65 |
| Found | 58.23 | 4.94 | 9.64 |

MS (EI, 70 eV): 290 (M+), 216, 132, 91, 77, 65, 56, 29.
IR (KBr): 2980, 1745, 1720, 1440, 1420, 1400, 1225, 1140.
NMR(DMSO-d$_6$/TMS): δ=1.21(t,3H,J=7.1 Hz), 4.17(q,2H,J=7.1 Hz), 4.41(s,2H), 4.75(s,2H), 7.31-7.47(m,5H).
Ethyl 1-(2-methylbenzyl)-2,4,5-trioxoimidazolidine-3-acetate (Compound 7)
m.p.: 158°–160° C.
Elementary Analysis: C$_{15}$H$_{16}$N$_2$O$_5$

|  | C % | H % | N % |
| --- | --- | --- | --- |
| Calculated | 59.21 | 5.30 | 9.21 |
| Found | 59.07 | 5.47 | 9.07 |

MS (EI, 70eV): 304 (M+), 286, 147, 146, 105, 104, 91, 77, 56, 29.
IR (KBr): 2980, 2950, 1720, 1445, 1425, 1400, 1220, 1140.
NMR(DMSO-$d_6$/TMS): $\delta$=1.20(t,3H,J=7.1 Hz), 2.34(s,3H), 4.16(q,2H,J=7.1 Hz), 4.42(s,2H), 4.72(s,2H), 7.14–7.25(m,5H).
Ethyl 1-(4-methylbenzyl)-2,4,5-trioxoimidazolidine-3-acetate (Compound 8)
m.p.: 117.5°–118.5° C.
Elementary Analysis: $C_{15}H_{16}N_2O_5$

|  | C % | H % | N % |
|---|---|---|---|
| Calculated | 59.21 | 5.30 | 9.21 |
| Found | 59.04 | 5.39 | 9.15 |

MS (EI, 70 eV): 304 (M+), 147, 146, 132, 118, 105, 91, 77, 56, 29.
IR (KBr): 2980, 2950, 1750, 1725, 1445, 1420, 1440, 1230, 1145.
NMR(DMSO-$d_6$/TMS): $\delta$=1.20(t,3H,J=7.1 Hz), 2.28(s,3H), 4.16(q,2H,J=7.1 Hz), 4.41(s,2H), 4.69(s,2H), 7.16 and 7.22(each d,4H,J=8.3 Hz).
Ethyl 1-(2-methoxylbenzyl)-2,4,5-trioxoimidazolidine-3-acetate (Compound 9)
m.p.: 121°–122° C.
Elementary Analysis: $C_{15}H_{16}N_2O_6$

|  | C % | H % | N % |
|---|---|---|---|
| Calculated | 56.25 | 5.03 | 8.75 |
| Found | 56.45 | 5.12 | 8.75 |

MS (EI, 70 eV): 320 (M+), 218, 162, 148, 134, 121, 102, 91, 78, 77, 65, 56, 29.
IR (KBr): 2980, 2945, 2830, 1720, 1445, 1405, 1220, 1140.
NMR(DMSO-$d_6$/TMS): $\delta$=1.20(t,3H,J=7.1 Hz), 3.80(s,3H), 4.16(q,2H,J=7.1 Hz), 4.42(s,2H), 4.70(s,2H), 6.89–7.31(m,4H).
Ethyl 1-(3-methoxylbenzyl)-2,4,5-trioxoimidazolidine-3-acetate (Compound 10)
m.p.: 116°–117° C.
Elementary Analysis: $C_{15}H_{16}N_2O_6$

|  | C % | H % | N % |
|---|---|---|---|
| Calculated | 56.25 | 5.03 | 8.75 |
| Found | 56.30 | 5.14 | 8.70 |

MS (EI, 70 eV): 320 (M+), 163, 162, 148, 134, 121, 102, 91, 78, 77, 65, 56, 29.
IR (KBr): 3030, 2945, 2830, 1750, 1720, 1440, 1420, 1400, 1220, 1140.
NMR(DMSO-$d_6$/TMS): $\delta$=1.20(t,3H,J=7.1 Hz), 3.74(s,3H), 4.16(q,2H,J=7.1 Hz), 4.42(s,2H), 4.72(s,2H), 6.89–7.29(m,4H).
Ethyl 1-(3,4-dimethoxylbenzyl)-2,4,5-trioxoimidazolidine-3-acetate (Compound 11)
m.p.: 118°–123° C.
Elementary Analysis: $C_{16}H_{18}N_2O_7$

|  | C % | H % | N % |
|---|---|---|---|
| Calculated | 54.86 | 5.18 | 8.00 |
| Found | 54.73 | 5.19 | 7.82 |

MS (EI, 70 eV): 350 (M+), 192, 178, 162, 151, 135, 107, 77, 65, 56, 29.
IR (KBr): 2980, 2950, 2840, 1750, 1725, 1445, 1420, 1220, 1140.
NMR(DMSO-$d_6$/TMS): $\delta$=1.20(t,3H,J=7.1 Hz), 3.73(2×s,each 3H), 4.16(q,2H,J=7.1 Hz), 4.41(s,2H), 4.67(s,2H), 6.85(dd,1H,J=8.3, 2.0 Hz), 6.91(d,1H,J=8.3 Hz), 6.92(d,1H,J=2.0 Hz).
Ethyl 1-(2-chlorobenzyl)-2,4,5-trioxoimidazolidine-3-acetate (Compound 12)
m.p.: 142°–143° C.
Elementary Analysis: $C_{14}H_{13}N_2O_5Cl$

|  | C % | H % | N % |
|---|---|---|---|
| Calculated | 51.78 | 4.04 | 8.63 |
| Found | 51.91 | 4.12 | 8.48 |

MS (EI, 70 eV): 324 ($M^{30}$), 289, 166, 132, 125, 102, 89, 70, 56, 29.
IR (KBr): 2980, 2940, 2900, 1745, 1725, 1440, 1420, 1400, 1220, 1140.
NMR(DMSO-$d_6$/TMS): $\delta$=1.21(t,3H,J=7.1 Hz), 4.17(q,2H,J=7.1 Hz), 4.43(s,2H), 4.82(s,2H), 7.32–7.51(m,4H).
Ethyl 1-(3-chlorobenzyl)-2,4,5-trioxoimidazolidine-3-acetate (Compound 13)
m.p.: 136°–137° C.
Elementary Analysis: $C_{14}H_{13}N_2O_5Cl$

|  | C % | H % | N % |
|---|---|---|---|
| Calculated | 51.78 | 4.04 | 8.63 |
| Found | 51.89 | 4.07 | 8.58 |

MS (EI, 70 eV): 324 (M+), 250, 166, 132, 125, 102, 89, 70, 59, 29.
IR (KBr): 2980, 2940, 1725, 1440, 1420, 1400, 1220, 1140.
NMR(DMSO-$d_6$/TMS): $\delta$=1.20(t,3H,J=7.1 Hz), 4.17(q,2H,J=7.1 Hz), 4.41(s,2H), 4.77(s,2H), 7.31–7.46(m,4H).
Ethyl 1-(4-clorobenzyl)-2,4,5-trioxoimidazolidine-3-acetate (Compound 14)
m.p.: 130°–131° C.
Elementary Analysis: $C_{14}H_{13}N_2O_5Cl$

|  | C % | H % | N % |
|---|---|---|---|
| Calculated | 51.78 | 4.04 | 8.62 |
| Found | 51.91 | 4.04 | 8.56 |

MS (EI, 70 eV): 324 (M+), 250, 166, 132, 125, 102, 89, 70, 56, 29.
IR (KBr): 2980, 1740, 1720, 1440, 1420, 1225, 1140.
NMR(DMSO-$d_6$/TMS): $\delta$=1.20(t,3H,J=7.1 Hz), 4.16(q,2H,J=7.1 Hz), 4.41(s,2H), 4.77(s,2H), 7.38 and 7.42(each d,4H,J=8.3 Hz).
Ethyl 1-(4-bromobenzyl)-2,4,5-trioxoimidazolidine-3-acetate (Compound 15)
m.p.: 143°–144° C.
Elementary Analysis: $C_{14}H_{13}N_2O_5Br$

|  | C % | H % | N % |
|---|---|---|---|
| Calculated | 45.55 | 3.55 | 7.59 |
| Found | 45.54 | 3.58 | 7.53 |

MS (EI, 70 eV): 368 (M+), 294, 210, 169, 132, 102, 90, 89, 56, 29.
IR (KBr): 2980, 2950, 1745, 1720, 1440, 1420, 1400, 1230, 1145.
NMR(DMSO-d$_6$/TMS): δ=1.20(t,3H,J=7.1 Hz), 4.16(q,2H,J=7.1 Hz), 4.41(s,2H), 4.72(s,2H), 7.31 and 7.56(each d,1H,J=8.4 Hz).
Ethyl 1-(4-fluorobenzyl)-2,4,5-trioxoimidazolidine-3-acetate (Compound 16)
m.p.: 102°–104° C.
Elementary Analysis: C$_{14}$H$_{13}$N$_2$O$_5$F

|  | C % | H % | N % |
|---|---|---|---|
| Calculated | 54.55 | 4.25 | 9.09 |
| Found | 54.55 | 4.26 | 9.08 |

MS (EI, 70 eV). 308 (M+), 234, 150, 109, 102, 83, 70.
IR (KBr): 2980, 2950, 1740, 1720, 1440, 1420, 1400, 1235, 1220, 1140.
NMR(DMSO-d$_6$/TMS): δ=1.20(t,3H,J=7.11 Hz), 4.16(q,2H,J=7.1 Hz), 4.40(s,2H), 4.74(s,2H), 7.17–7.42(m,5H).
Ethyl 1-(2,4-dichlorobenzyl)-2,4,5-trioxoimidazolidine-3-acetate (Compound 17)
m.p.: 170°–171° C.
Elementary Analysis: C$_{14}$H$_{12}$N$_2$O$_5$Cl$_2$

|  | C % | H % | N % |
|---|---|---|---|
| Calculated | 46.82 | 3.37 | 7.80 |
| Found | 46.88 | 3.38 | 7.79 |

MS (EI, 70 eV): 358 (M+), 323, 284, 200, 166, 159, 123, 102, 89, 70, 56, 29.
IR (KBr): 2980, 2945, 1750, 1725, 1445, 1420, 1400, 1225, 1145.
NMR(DMSO-d$_6$/TMS): δ=1.21(t,3H,J=7.1 Hz), 4.17(q,2H,J=7.1 Hz), 4.43(s,2H), 4.80(s,2H), 7.44(dd,1H,J=8.3, 2.0 Hz), 7.53(d,1H,J=8.3 Hz), 7.66(d,1H,J=2.0 Hz).
Ethyl 1-(3,4-dichlorobenzyl)-2,4,5-trioxoimidazolidine-3-acetate (Compound 18)
m.p.: 136°–137° C.
Elementary Analysis: C$_{14}$H$_{12}$N$_2$O$_5$Cl$_2$

|  | C % | H % | N % |
|---|---|---|---|
| Calculated | 46.82 | 3.37 | 7.80 |
| Found | 46.94 | 3.32 | 7.81 |

MS (EI, 70 eV): 358 (M+), 284, 200, 166, 159, 123, 102, 89, 70, 56, 29.
IR (KBr): 2980, 2950, 1750, 1725, 1450, 1425, 1400, 1235, 1150.
NMR(DMSO-d$_6$/TMS): δ=1.21(t,3H,J=7.1 Hz), 4.17(q,2H,J=7.11 Hz), 4.41(s,2H), 4.77(s,2H), 7.36(dd,1H,J=8.3, 2.0 Hz), 7.63(d,1H,J=8.3 Hz), 7.66(d,1H,J=2.0 Hz).
Ethyl 1-(3-nitrobenzyl)-2,4,5-trioxoimidazolidine-3-acetate (Compound 19)
m.p.: 124.5°–125.5° C.
Elementary Analysis: C$_{14}$H$_{13}$N$_3$O$_7$

|  | C % | H % | N % |
|---|---|---|---|
| Calculated | 50.15 | 3.91 | 12.53 |
| Found | 50.40 | 3.79 | 12.62 |

MS (EI, 70 eV): 335 (M+), 318, 262, 233, 161, 136, 90, 89, 77, 70, 56, 29.
IR (KBr): 3070, 2980, 2950, 1740, 1720, 1525, 1350, 1220, 1145.
NMR(DMSO-d$_6$/TMS): δ=1.21(t,3H,J=7.2 Hz), 4.17(q,2H,J=7.2 Hz), 4.41(s,2H), 4.91(s,2H), 7.64–8.26(m,4H).
Ethyl 1-(2-phenylethyl)-2,4,5-trioxoimidazolidine-3-acetate (Compound 20)
m.p.: 106°–108° C.
Elementary Analysis: C$_{15}$H$_{16}$N$_2$O$_5$

|  | C % | H % | N % |
|---|---|---|---|
| Calculated | 59.21 | 5.30 | 9.21 |
| Found | 58.94 | 5.44 | 8.88 |

MS (EI, 70 eV): 304 (M+), 231, 160, 104, 91, 77, 65, 56, 29.
IR (KBr): 3030, 2960, 2930, 1720, 1440, 1430, 1410, 1230, 1135.
NMR(DMSO-d$_6$/TMS): δ=1.21(t,3H,J=7.1 Hz), 2.89(t,2H,J=7.4 Hz), 3.77(t,2H,J=7.4 Hz), 4.17(q,2H,J=7.1 Hz), 4.39(s,2H), 7.20–7.31(m,5H).
Ethyl 1-(2-(4-methylphenyl)ethyl)-2,4,5-trioxoimidazolidine-3-acetate (Compound 21)
m.p.: 98°–99° C.
Elementary Analysis: C$_{16}$H$_{18}$N$_2$O$_5$

|  | C % | H % | N % |
|---|---|---|---|
| Calculated | 60.37 | 5.70 | 8.80 |
| Found | 59.84 | 5.88 | 8.52 |

MS (EI, 70 eV): 318 (M+), 118, 105, 91, 77, 65, 56, 29.
IR (KBr): 2950, 2920, 2850, 1750, 1720, 1450, 1410, 1230, 1130.
NMR(DMSO-d$_6$/TMS): δ=1.21(t,3H,J=7.1 Hz), 2.26(s,3H), 2.84(t,2H,J=7.4 Hz), 3.73(t,2H,J=7.4 Hz), 4.17(q,2H,J=71. Hz), 4.39(s,2H), 7.10(s,5H).
Ethyl 1-(2-(3,4-dimethoxyphenyl)ethyl)-2,4,5-trioxoimidazolidine-3-acetate (Compound 22)
m.p.: 141°–142° C.
Elementary Analysis: C$_{17}$H$_{20}$N$_2$O$_7$

|  | C % | H % | N % |
|---|---|---|---|
| Calculated | 56.04 | 5.53 | 7.69 |
| Found | 55.67 | 5.65 | 7.42 |

MS (EI, 70 eV): 364 (M+), 164, 151, 91, 77, 65, 56, 29.
IR (KBr): 3000, 2950, 2840, 1745, 1720, 1440, 1430, 1405, 1215, 1145.
NMR(DMSO-d$_6$/TMS): δ=1.21(t,3H,J=7.1 Hz), 2.82(t,2H,J=7.2 Hz), 3.71 and 3.73(each s,6H), 4.16(q,2H,J=7.1 Hz), 4.39(s,2H), 6.71(dd,1H,J=8.3, 2.0 Hz), 6.81(d,1H,J=2.0 Hz), 6.84(d,11H,J=8.3 Hz)
Ethyl 1-(2-(2-chlorophenyl)ethyl)-2,4,5-trioxoimidazolidine-3-acetate (Compound 23)
m.p.: 140°–141° C.
Elementary Analysis: C$_{15}$H$_{15}$N$_2$O$_5$Cl

|  | C % | H % | N % |
|---|---|---|---|
| Calculated | 53.19 | 4.46 | 8.27 |
| Found | 52.92 | 4.56 | 8.15 |

MS (EI, 70 eV): 338 (M+), 138, 125, 103, 89, 77, 56, 29.

IR (KBr): 3000, 2950, 1720, 1445, 1430, 1410, 1230, 1140.

NMR(DMSO-$d_6$/TMS): $\delta$=1.21(t,3H,J=7.1 Hz), 3.03(t,2H,J=7.2 Hz), 3.80(t,2H,J=7.2 Hz), 4.17(q,2H,J=7.1 Hz), 4.39(s,2H), 7.25–7.44(m,5H).

Ethyl 1-(2-(4-bromophenyl)ethyl)-2,4,5-trioxoimidazolidine-3-acetate (Compound 24)

m.p.: 112.5°–113.5° C.

Elementary Analysis: $C_{15}H_{15}N_2O_5Br$

|  | C % | H % | N % |
|---|---|---|---|
| Calculated | 47.02 | 3.95 | 7.31 |
| Found | 47.19 | 4.05 | 7.21 |

MS (EI, 70 eV): 382, 384 (M+), 309, 311, 238, 240, 182, 184, 169, 171, 103, 90, 77, 56, 29.

IR (KBr): 2950, 1725, 1440, 1420, 1400, 1240, 1140.

NMR (DMSO-$d_6$/TMS): $\delta$=1.21(t,3H,J=7.2 Hz), 2.88(t,2H,J=6.9 Hz), 3.77(t,2H,J=6.9 Hz), 4.17(q,2H,J=7.2 Hz), 4.39(s,2H), 7.20, 7.47(each d,4H,J=8.3 Hz).

Ethyl 1-(2-(3,4-dichlorophenyl)ethyl)-2,4,5-trioxoimidazolidine-3-acetate (Compound 25)

m.p.: 104°–105° C.

Elementary Analysis: $C_{15}H_{14}N_2O_5Cl_2$

|  | C % | H % | C % |
|---|---|---|---|
| Calculated | 48.28 | 3.78 | 7.51 |
| Found | 48.19 | 3.82 | 7.50 |

MS (EI, 70 eV): 372 (M+), 172, 159, 123, 102, 89, 56, 29.

IR (KBr): 2940, 1725, 1440, 1405, 1220, 1140.

NMR(DMSO-$d_6$/TMS): $\delta$=1.20(t,3H,J=7.2 Hz), 2.91(t,2H,J=6.9 Hz), 3.80(t,2H,J=6.9 Hz), 4.16(q,2H,J=7.2 Hz), 4.38(s,2H), 7.23(dd,1H,J=8.3, 2.0 Hz), 7.53(d,1H,J=8.3 Hz), 7.56(d,1H,J=2.0 Hz).

Ethyl 1-(2-(3-nitrophenyl)ethyl)-2,4,5-trioxoimidazolidine-3-acetate (Compound 26)

m.p.: 102°–104° C.

Elementary Analysis: $C_{15}H_{15}N_3O_7$

|  | C % | H % | N % |
|---|---|---|---|
| Calculated | 51.58 | 4.33 | 12.03 |
| Found | 51.83 | 4.35 | 12.20 |

MS (EI, 70 eV): 349 (M+), 332, 276, 149, 136, 103, 90, 77, 56, 29.

IR (KBr): 3300, 2990, 2945, 1780, 1720, 1520, 1445, 1340, 1225, 1140.

NMR(DMSO-$d_6$/TMS): $\delta$=1.20(t,3H,J=7.2 Hz), 3.07(t,2H,J=6.9 Hz), 3.87(t,2H,J=6.9 Hz), 4.15(q,2H,J=7.2 Hz), 4.37(s,2H), 7.56–8.15(m,4H).

Ethyl 1-(3-phenylpropyl)-2,4,5-trioxoimidazolidine-3-acetate (Compound 27)

m.p.: 93°–94° C.

Elementary Analysis: $C_{16}H_{18}N_2O_5$

|  | C % | H % | N % |
|---|---|---|---|
| Calculated | 60.37 | 5.70 | 8.80 |
| Found | 60.14 | 5.87 | 8.70 |

MS (EI, 70 eV): 318 (M+), 201, 140, 118, 117, 105, 102, 91, 56, 29.

IR (KBr): 3000, 2950, 2930, 1720, 1450, 1430, 1410, 1230, 1140.

NMR(DMSO-$d_6$/TMS): $\delta$=1.21(t,3H,J=7.1 Hz), 1.88(q,2H,J=7.4 Hz), 2.61(t,2H,J=7.4 Hz), 3.57(t,2H,J=7.4 Hz), 4.17(q,2H,J=7.1 Hz), 4.39(s,2H), 7.16–7.30(m,5H).

Ethyl 1-(4-phenylbutyl)-2,4,5-trioxoimidazolidine-3-acetate (Compound 28)

m.p.: 92.5°–94° C.

Elementary Analysis: $C_{17}H_{20}N_2O_5$

|  | C % | H % | N % |
|---|---|---|---|
| Calculated | 61.44 | 6.07 | 8.43 |
| Found | 61.28 | 6.23 | 8.31 |

MS (EI, 70 eV): 332 (M+), 314, 130, 117, 104, 91, 65, 56, 29.

IR (KBr): 2980, 2930, 2850, 1725, 1450, 1430, 1410, 1230, 1140.

NMR(DMSO-$d_6$/TMS): $\delta$=1.20(t,3H,J=7.1 Hz), 1.58(m,4H), 2.59(m,2H), 3.56(m,2H), 4.15(q,2H,J=7.1), 4.38(s,2H), 7.14–7.29(m,5H).

Ethyl 1-(3,4-dichlorobenzyl)-2,4,5-trioxoimidazolidine-3-acetate (Compound 29)

EXAMPLE 2

2.9 g of Compound 1 was added to a mixture of 8 ml of acetic acid and 4 ml of concentrated hydrochloric acid. After heating under refluxed 2 hours, about the half of solvent was distilled away. 4 ml of acetic acid and 2 ml of concentrated hydrochloric acid were further added thereto and the solution was heated under reflux for 2 hours. The residue obtained by distillation of the solvent was dissolved in ethyl acetate, washed with water and extracted with 10% sodium carbonate. After washing with ethyl acetate, the solution was acidified with concentrated hydrochloric acid. Precipitated crystals were extracted with ethyl acetate, washed with water and brine, dried over anhydrous sodium sulfate and concentrated to dryness. Ether was added to the residue, and the residue was collected by filtration and recrystallized from ethyl acetate/hexane to give 0.9 g of 3-carboxymethyl-1-methylparabanic acid (Compound 30).

m.p.: 191°–193° C.

Elementary Analysis: $C_6H_6N_2O_5$

|  | C % | H % | N % |
|---|---|---|---|
| Calculated | 38.72 | 3.25 | 15.05 |
| Found | 38.73 | 3.26 | 14.93 |

MS (EI, 70 eV): 186 (M+), 142, 113, 70, 58, 57, 56, 45, 29.

IR (KBr): 3000–2400, 1780, 1730, 1710, 1460, 1425, 1390, 1260, 1145.

NMR(DMSO-$d_6$/TMS): $\delta$=3.03(s,3H), 4.28(s,2H), 13.33(bs,1H).

The following compounds were obtained in the same manner.

1-Butyl-3-carboxymethylparabanic acid (Compound 31)
m.p.: 123°–124° C.
Elementary Analysis: $C_9H_{12}N_2O_5$

|  | C % | H % | N % |
|---|---|---|---|
| Calculated | 47.37 | 5.30 | 12.28 |
| Found | 47.42 | 5.56 | 12.15 |

MS (EI, 70 eV): 228 (M+), 186, 173, 155, 140, 127, 102, 74, 70, 56, 41, 29, 27.
IR (KBr): 3000–2400, 1770, 1730, 1720, 1450, 1430, 1405, 1250, 1135.
NMR(DMSO-$d_6$/TMS) $\delta$=0.88(t,3H,J=7.4 Hz), 1.29(sex,2H,J=7.4 Hz), 1.55(quin,2H,J=7.4 Hz), 3.54(t,2H,J=7.4 Hz), 4.28(s,2H), 13.40(bs,1H).

3-Carboxymethyl-1-isobutylparabanic acid (Compound 32)
m.p.: 162°–163° C.
Elementary Analysis: $C_9H_{12}N_2O_5$

|  | C % | H % | N % |
|---|---|---|---|
| Calculated | 47.37 | 5.30 | 12.28 |
| Found | 47.42 | 5.59 | 12.07 |

MS (EI, 70 eV): 228 (M+), 186, 173, 155, 140, 127, 102, 84, 74, 70, 56, 43, 41, 27.
IR (KBr): 3000–2500, 1770, 1720, 1440, 1405, 1225, 1140.
NMR(DMSO-$d_6$/TMS): $\delta$=0.88(d,6H,J=6.9 Hz), 1.95(m,1H), 3.36(d,2H,J=6.9 Hz), 4.28(s,2H), 13.41(bs,1H).

3-Carboxymethyl-1-hexylparabanic acid (Compound 33)
m.p.: 104°–106° C.
Elementary Analysis: $C_{11}H_{16}N_2O_5$

|  | C % | H % | N % |
|---|---|---|---|
| Calculated | 51.56 | 6.29 | 10.93 |
| Found | 51.73 | 6.72 | 10.93 |

MS (EI, 70 eV): 256 (M+), 186, 173, 155, 140, 127, 102, 84, 74, 56, 55, 43, 41, 29, 27.
IR (KBr): 3000–2500, 2950, 2920, 2850, 1770, 1730, 1710, 1445, 1430, 1400, 1250, 1135.
NMR(DMSO-$d_6$/TMS): $\delta$=0.86(m,3H), 1.26(m,6H), 1.57(m,2H), 3.53(t,2H,J=7.1HZ), 4.27(s,2H), 13.41(bs,1H).

3-Carboxymethyl-1-(4-methylcyclohexyl)parabanic acid (Compound 34)
m.p.: 190.5°–191.5° C.
Elementary Analysis: $C_{12}H_{16}N_2O_5$

|  | C % | H % | N % |
|---|---|---|---|
| Calculated | 53.73 | 6.01 | 10.44 |
| Found | 53.67 | 5.99 | 10.71 |

MS (EI, 70 eV): 268 (M+), 174, 155, 127, 96, 81, 67, 55,
IR (KBr): 3000–2500, 2950, 2925, 2860, 1770, 1720, 1440, 1260, 1140.
NMR(DMSO-$d_6$/TMS): $\delta$=0.88(d,3H,J=6.5 Hz), 1.02(m,2H), 1.37(m,2H), 1.73(m,4H), 1.97(m,2H), 3.88(m,1H), 4.31(s,2H), 13.17(bs,1H).

1-Benzyl-3-carboxymethylparabanic acid (Compound 35)
m.p.: 207.5°–209.5° C.
Elementary Analysis: $C_{12}H_{10}N_2O_5$

|  | C % | H % | N % |
|---|---|---|---|
| Calculated | 54.97 | 3.84 | 10.68 |
| Found | 55.15 | 3.87 | 10.65 |

MS (EI, 70eV): 262 (M+), 133, 104, 91, 77, 65, 56.
IR (KBr): 3000–2500, 1730, 1710, 1440, 1425, 1400, 1260, 1145.
NMR(DMSO-$d_6$/TMS): $\delta$=4.30(s,2H), 4.74(s,2H), 7.34(m,4H), 13.40(bs,1H).

3-Carboxymethyl-1-(2-methylbenzyl)parabanic acid (Compound 36)
m.p.: 198°–199° C.
Elementary Analysis: $C_{13}H_{12}N_2O_5$

|  | C % | H % | N % |
|---|---|---|---|
| Calculated | 56.52 | 4.38 | 10.14 |
| Found | 56.88 | 4.48 | 10.15 |

MS (EI, 70 eV): 276 (M+), 147, 132, 104, 91, 77.
IR (KBr): 3000–2400, 1770, 1725, 1710, 1440, 1425, 1400, 1240, 1145.
NMR(DMSO-$d_6$/TMS): $\delta$=2.35(s,3H), 4.31(s,2H), 3-Carboxymethyl-1-(4-methylbenzyl)parabanic acid (Compound 37)
m.p.: 192°–193.5° C.
Elementary Analysis: $C_{13}H_{12}N_2O_5$

|  | C % | H % | N % |
|---|---|---|---|
| Calculated | 56.52 | 4.38 | 10.14 |
| Found | 56.61 | 4.41 | 10.02 |

MS (EI, 70 eV): 276 (M+), 147, 132, 118, 105, 91, 77, 56.
IR (KBr): 3000–2500, 1770, 1735, 1715, 1450, 1425, 1400, 1245, 1145.
NMR(DMSO-$d_6$/TMS): $\delta$=2.28(s,3H), 4.29(s,2H), 4.69(s,2H), 7.16 and 7.22(each d,4H,J=8.4 Hz), 3.43(bs,1H).

3-Carboxymethyl-1-(2-methoxybenzyl)parabanic acid (Compound 38)
m.p.: 185°–186° C.
Elementary Analysis: $C_{13}H_{12}N_2O_6$

|  | C % | H % | N % |
|---|---|---|---|
| Calculated | 53.43 | 4.14 | 9.59 |
| Found | 53.14 | 4.02 | 9.46 |

MS (EI, 70 eV): 292 (M+), 218, 162, 148, 134, 121, 107, 91, 77, 65, 56.
IR (KBr): 3000–2400, 1770, 1720, 1710, 1445, 1430, 1400, 1245, 1145.
NMR(DMSO-$d_6$/TMS): $\delta$=3.80(s,3H), 4.31(s,2H), 4.69(s,2H), 6.89–7.31(m,4H), 13.44(bs,1H).

3-Carboxymethyl-1-(3-methoxybenzyl)parabanic acid (Compound 39)
m.p.: 189°–190° C.

Elementary Analysis: $C_{13}H_{12}N_2O_6$

|  | C % | H % | N % |
|---|---|---|---|
| Calculated | 53.43 | 4.14 | 9.59 |
| Found | 53.31 | 3.99 | 9.62 |

MS (EI, 70 eV): 292 (M+), 163, 148, 134, 121, 105, 91, 77, 65, 56.

IR (KBr): 3000–2500, 1765, 1730, 1710, 1445, 1425, 1400, 1245, 1145.

NMR(DMSO-$d_6$/TMS): δ=3.74(s,3H), 4.30(s,2H), 4.72(s,2H), 6.86–7.29(m,4H), 13.45(bs,1H).

3-Carboxymethyl-1-(3,4-dimethoxybenzyl)parabanic acid (Compound 40)

m.p.: 163°–164° C.

Elementary Analysis: $C_{14}H_{14}N_2O_7$

|  | C % | H % | N % |
|---|---|---|---|
| Calculated | 52.18 | 4.38 | 8.69 |
| Found | 52.21 | 4.71 | 8.30 |

MS (EI, 70 eV): 322 (M+), 192, 178, 162, 151, 135, 107, 56.

IR (KBr): 3350, 2930, 1760, 1720, 1450, 1405, 1255, 1145.

NMR(DMSO-$d_6$/TMS): δ=3.73(s,6H), 4.30(s,2H), 4.67(s,2H), 6.86(dd,1H,J=8.4, 2.0 Hz), 6.90(d,1H,J=2.0 Hz), 6.92(d,1H,J=8.4 Hz), 13.46{bs,1H}.

3-Carboxymethyl-1-(2-chlorobenzyl)parabanic acid (Compound 41)

m.p.: 227°–228° C.

Elementary Analysis: $C_{12}H_9N_2O_5Cl$

|  | C % | H % | N % |
|---|---|---|---|
| Calculated | 48.58 | 3.06 | 9.44 |
| Found | 48.44 | 2.86 | 9.76 |

MS (EI, 70 eV): 296 (M+), 261, 166, 138, 132, 125, 89, 77, 63, 56.

IR (KBr): 3000–2400, 1770, 1710, 1430, 1420, 1390, 1260, 1145.

NMR(DMSO-$d_6$/TMS): δ=4.33(s,2H), 4.82(s,2H), 7.32–7.51(m,4H), 13.44(bs,1H).

3-Carboxymethyl-1-(3-chlorobenzyl)parabanic acid (Compound 42)

m.p.: 207°–208° C.

Elementary Analysis: $C_{12}H_9N_2O_5Cl$

|  | C % | H % | N % |
|---|---|---|---|
| Calculated | 48.58 | 3.06 | 9.44 |
| Found | 48.43 | 2.84 | 9.65 |

MS (EI, 70 eV): 296 (M+), 250, 167, 132, 125, 89, 77, 74, 63, 56.

IR (KBr): 3000–2400, 1770, 1720, 1440, 1425, 1400, 1250, 1150.

NMR(DMSO-$d_6$/TMS): δ=4.30(s,2H), 4.77(s,2H), 7.31–7.45(m,4H), 13.46(bs,1H).

3-Carboxymethyl-1-(4-chlorobenzyl)parabanic acid (Compound 43)

m.p.: 185°–186° C.

Elementary Analysis: $C_{12}H_9N_2O_5Cl$

|  | C % | H % | N % |
|---|---|---|---|
| Calulated | 48.58 | 3.06 | 9.44 |
| Found | 48.23 | 2.93 | 9.64 |

MS (EI, 70 eV): 296 (M+), 167, 132, 125, 89, 77, 74, 63, 56.

IR (KBr): 3000–2500, 1780, 1740, 1720, 1440, 1405, 1250, 1150.

NMR(DMSO-$d_6$/TMS): δ=4.29(s,2H$_0$, 4.74(s,2H), 7.37 and 7.43(each d,4H,J=8.4 Hz), 13.46(bs,1H).

1-(4-Bromobenzyl)-3-carboxymethylparabanic acid (Compound 44)

m.p.: 200.5°–201.5° C.

Elementary Analysis: $C_{12}H_9N_2O_5Br$

|  | C % | H % | N % |
|---|---|---|---|
| Calculated | 42.25 | 2.66 | 8.21 |
| Found | 42.37 | 2.58 | 8.39 |

MS (EI, 70 eV): 340, 342 (M+), 294, 296, 211, 213, 182, 184, 169, 171, 132, 90, 89, 77, 74, 56.

IR (KBr): 2950, 2400, 1770, 1730, 1700, 1435, 1420, 1400, 1240, 1140.

NMR(DMSO-$d_6$/TMS): δ=4.30(s,2H), 4.72(s,2H), 7.31 and 7.56(each d,4H,J=8.4 Hz), 13.41(bs,1H).

3-Carboxymethyl-1-(4-fluorobenzyl)parabanic acid (Compound 45)

m.p.: 173°–174° C.

Elementary Analysis: $C_{12}H_9N_2O_5F$

|  | C % | H % | N % |
|---|---|---|---|
| Calculated | 51.44 | 3.24 | 10.00 |
| Found | 51.65 | 3.19 | 9.99 |

MS (EI, 70 eV): 280 (M+), 151, 122, 109, 95, 83, 74, 56.

IR (KBr): 3000–2400, 1770, 1730, 1710, 1440, 1420, 1400, 1255, 1140.

NMR(DMSO-$d_6$/TMS): δ=4.30(s,2H), 4.74(s,2H), 7.17–7.42(m,4H), 13.43(bs,1H).

3-Carboxymethyl-1-(2,4-dichlorobenzyl)parabanic acid (Compound 46)

m.p.: 230.5°–232° C.

Elementary Analysis: $C_{12}H_8N_2O_5Cl_2$

|  | C % | H % | N % |
|---|---|---|---|
| Calculated | 43.53 | 2.44 | 8.46 |
| Found | 43.47 | 2.28 | 8.64 |

MS (EI, 70 eV): 330 (M+), 295, 284, 166, 159, 123, 102, 74, 56.

IR (KBr): 3000–2500, 1780, 1735, 1720, 1450, 1430, 1390, 1255, 1150.

NMR(DMSO-$d_6$/TMS): δ=4.31(s,2H), 4.80(s,2H), 7.44(dd,1H,J=8.4, 2.0 Hz), 7.52(d,1H,J=8.4 Hz), 7.67(d,1H,J=2.0 Hz), 13.43(bs,1H).

3-Carboxymethyl-1-(3,4-dichlorobenzyl)parabanic acid (Compound 47)

m.p.: 196.5°–197.5° C.

Elementary Analysis: $C_{12}H_8N_2O_5Cl_2$

|  | C % | H % | N % |
|---|---|---|---|
| Calculated | 43.53 | 2.44 | 8.46 |
| Found | 43.36 | 2.14 | 8.48 |

MS (EI, 70 eV): 330 (M+), 248, 201, 166, 159, 123, 102, 89, 74, 56.

IR (KBr): 3000–2400, 1780, 1730, 1710, 1440, 1420, 1390, 1255, 1150.

NMR(DMSO-$d_6$/TMS) δ=4.30(s,2H), 4.77(s,2H), 7.36(dd,1H,J=8.4, 2.0 Hz), 7.63(d,1H,J=8.4 Hz), 7.66(d,1H,J=2.0 Hz), 13.44(bs,1H).

3-Carboxymethyl-1-(3-nitrobenzyl)parabanic acid (Compound 48)

m.p.: 192°–194° C.

Elementary Analysis: $C_{12}H_9N_3O_7$

|  | C % | H % | N % |
|---|---|---|---|
| Calculated | 46.91 | 2.95 | 13.68 |
| Found | 47.15 | 2.88 | 13.98 |

MS (EI, 70 eV): 307 (M+), 290, 263, 233, 177, 161, 136, 90, 89, 77, 70, 56.

IR (KBr): 3000–2400, 1725, 1705, 1525, 1440, 1420, 1400, 1340, 1250, 1145.

NMR(DMSO-$d_6$/TMS): δ=4.30(s,2H), 4.91(s,2H), 7.65–8.25(m,4H), 13.42(bs,1H).

3-Carboxymethyl-1-(2-phenylethyl)parabanic acid (Compound 49)

m.p.: 154.5°–155.5° C.

Elementary Analysis: $C_{13}H_{12}N_2O_5$

|  | C % | H % | N % |
|---|---|---|---|
| Calculated | 56.52 | 4.38 | 10.14 |
| Found | 56.59 | 4.44 | 10.06 |

MS (EI, 70 eV): 276 (M.), 104, 91, 77, 65, 56.

IR (KBr): 3000–2500, 1775, 1720, 1710, 1440, 1425, 1400, 1240, 1140.

NMR(DMSO-$d_6$/TMS): δ=2.89(t,2H,J=7.2 Hz), 3.77(t,2H,J=7.2 Hz), 4.28(s,2H), 7.19–7.31(m,5H), 13.43(bs,1H).

3-Carboxymethyl-1-(2-(4-methylphenyl)ethyl)parabanic acid (Compound 50)

m.p.: 158°–159° C.

Elementary Analysis: $C_{14}H_{14}N_2O_5$

|  | C % | H % | N % |
|---|---|---|---|
| Calculated | 57.93 | 4.86 | 9.65 |
| Found | 57.95 | 5.05 | 9.55 |

MS (EI, 70 eV): 290 (M+), 118, 105, 77, 56.

IR (KBr): 3250, 2925, 1730, 1715, 1455, 1440, 1425, 1405, 1205, 1140.

NMR(DMSO-$d_6$/TMS): δ=2.26(s,3H), 2.84(t,2H,J=7.4 Hz), 3.73(t,2H,J=7.4 Hz), 4.29(s,2H), 7.10(s,4H), 13.46(bs,1H).

3-Carboxymethyl-1-(2-(3,4-dimethoxyphenyl)ethyl)-parabanic acid (Compound 51)

m.p.: 141°–142° C.

Elementary Analysis: $C_{15}H_{16}N_2O_7$

|  | C % | H % | N % |
|---|---|---|---|
| Calculated | 53.57 | 4.80 | 8.33 |
| Found | 53.28 | 4.91 | 8.21 |

MS (EI, 70 eV): 336 (M+), 164, 151, 107, 91, 77, 65, 56.

IR (KBr): 3250, 2930, 1725, 1440, 1425, 1405, 1260, 1140.

NMR(DMSO-$d_6$/TMS): δ=2.82(t,2H,J=7.2 Hz), 3.71(s,3H), 3.73(s,3H), 3.75(t,2H,J=7.2 Hz), 4.28(s,2H), 6.72(dd,1H,J=8.4, 2.0 Hz), 6.80(d,1H,J=2.0 Hz), 6.85(d,1H,J=8.4 Hz), 13.42(bs,1H).

3-Carboxymethyl-1-(2-(2-chlorophenyl)ethyl)parabanic acid (Compound 52)

m.p.: 148°–149° C.

Elementary Analysis: $C_{13}H_{11}N_2O_5Cl$

|  | C % | H % | N % |
|---|---|---|---|
| Calculated | 50.26 | 3.57 | 9.02 |
| Found | 50.28 | 3.56 | 9.02 |

MS (EI, 70 eV): 310 (M+), 138, 125, 103, 89, 77, 56.

IR (KBr): 3000–2500, 1770, 1725, 1710, 1440, 1425, 1405, 1250, 1140.

NMR(DMSO-$d_6$/TMS): δ=3.02(t,2H,J=7.2 Hz), 3.80(t,2H,J=7.2 Hz), 4.28(s,2H), 7.24–7.45(m,4H), 13.42(bs,1H).

1-(2-(4-Bromophenyl)ethyl)-3-carboxymethylparabanic acid (Compound 53)

m.p.: 172°–173° C.

Elementary Analysis: $C_{13}H_{11}N_2O_5Br$

|  | C % | H % | N % |
|---|---|---|---|
| Calculated | 43.97 | 3.12 | 7.89 |
| Found | 44.18 | 3.11 | 7.92 |

MS (EI, 70 eV): 354 (M+), 356, 182, 184, 169, 171, 103, 90, 77, 56.

IR (KBr): 3000–2500, 1770, 1720, 1435, 1400, 1250, 1140.

NMR(DMSO-$d_6$/TMS): δ=2.88(t,2H,J=6.9 Hz), 3.77(t,2H,J=6.9 Hz), 4.29(s,2H), 7.20, 7.46(each d,4H,J=8.4 Hz), 13.46(bs,1H).

3-Carboxymethyl-1-(2-(3,4-dichlorophenyl)ethyl)-parabanic acid (Compound 54)

m.p.: 136°–138° C.

Elementary Analysis: $C_{13}H_{11}N_2O_5Cl_2$

|  | C % | H % | N % |
|---|---|---|---|
| Calculated | 45.24 | 2.92 | 8.12 |
| Found | 45.33 | 2.96 | 8.12 |

MS (EI, 70 eV): 344 (M+), 172, 159, 89, 56.

IR (KBr): 3000–2500, 1770, 1730, 1710, 1445, 1430, 1405, 1210, 1140.

NMR(DMSO-$d_6$/TMS): δ=2.91(t,2H,J=6.9 Hz), 3.80(t,2H,J=6.9 Hz), 4.28(s,2H), 7.23(dd,1H,J=8.4, 2.0 Hz), 7.51(d,1H,J=8.4 Hz), 7.56(d,1H,J=2.0 Hz), 13.44(bs,1H).

3-Carboxymethyl-1-(2-(3-nitrophenyl)ethyl)parabanic acid (Compound 55)

m.p.: 139°–142° C.

Elementary Analysis: $C_{13}H_{11}N_3O_7$

|  | C % | H % | N % |
|---|---|---|---|
| Calculated | 48.60 | 3.45 | 13.18 |
| Found | 48.47 | 3.56 | 13.30 |

MS (EI, 70 eV): 321 (M+), 303, 149, 136, 103, 90, 77, 56.

IR (KBr): 3000-2500, 1725, 1520, 1440, 1420, 1400, 1250, 1140.

NMR(DMSO-$d_6$/TMS): $\delta = 3.06(t,2H,J=6.9$ Hz), 3.87(t,2H,J=6.9 Hz), 4.26(s,2H), 7.55-8.15(m,4H), 13.43(bs 1H).

3-Carboxymethyl-1-(3-phenylpropyl)parabanic acid (Compound 56)

m.p.: 145.5°-146.5° C.

Elementary Analysis: $C_{14}H_{14}N_2O_5$

|  | C % | H % | N % |
|---|---|---|---|
| Calculated | 57.93 | 4.86 | 9.65 |
| Found | 58.21 | 5.08 | 9.66 |

MS (EI, 70 eV): 290 (M+), 186, 173, 140, 118, 117, 105, 91, 77, 74, 65, 56.

IR (KBr): 3000-2400, 1775, 1725, 1705, 1440, 1410, 1255, 1135.

NMR(DMSO-$d_6$/TMS): $\delta = 1.88(tt,2H,J=7.2, 7.2$ Hz), 2.61(t,2H,J=7.2 Hz), 3.57(t,2H,J=7.2 Hz), 4.28(s,2H), 7.16-7.30(m,5H), 13.44(bs,1H).

3-Carboxymethyl-1-(4-phenylbutyl)parabanic acid (Compound 57)

m.p.: 102°-103° C.

Elementary Analysis: $C_{15}H_{16}N_2O_5$

|  | C % | H % | N % |
|---|---|---|---|
| Calculated | 59.21 | 5.30 | 9.21 |
| Found | 59.15 | 5.035 | 9.20 |

MS (EI, 70 eV): 304 (M+), 130, 117, 104, 91, 77, 65, 56.

IR (KBr): 3360, 2980, 2940, 1840, 1765, 1750, 1705, 1450, 1420, 1400, 1135.

NMR(DMSO-$d_6$/TMS): $\delta = 1.58(m,4H)$, 2.58(m,2H), 3.56(m,2H), 4.27(s,2H), 7.14-7.28(m,5H), 13.43(bs,1H).

3-Carboxypropyl-1-(3,4-dichlorobenzyl)parabanic acid (Compound 58)

m.p.: 118.5°-120° C.

Elementary Analysis: $C_{14}H_{12}N_2O_5Cl_2$

|  | C % | H % | N % |
|---|---|---|---|
| Calculated | 46.82 | 3.37 | 7.80 |
| Found | 46.51 | 3.38 | 7.54 |

MS (EI, 70 eV): 358 (M+), 340, 312, 284, 255, 200, 166, 159, 123, 112, 89, 70, 56.

IR (KBr): 3000-2500, 1730, 1700, 1440, 1410, 1400, 1245, 1130.

NMR(DMSO-$d_6$/TMS): $\delta = 1.79(quin,2H,J=6.9$ Hz), 2.32(t,2H,J=6.9 Hz), 3.54(t,2H,J=6.9 Hz), 4.69(s,2H), 7.39(dd,1H,J=8.4, 2.0 Hz), 7.61(d,1H,J=8.4 Hz), 7.69(d,1H,J=2.0 Hz), 12.10(bs,1H).

EXAMPLE 3

7.0 g of glycine ethyl ester hydrochloride was suspended in 100 ml of benzene, and 10 ml of phenylisocyanate and 8 ml of triethylamine were added thereto. The mixture was stirred for 5 hours and benzene was distilled away. Ethyl acetate was added to the residue, washed with water and brine, and dried over anhydrous sodium sulfate. Ethyl acetate was distilled away and 100 ml of 1N aqueous solution of sodium hydroxide was added to the resulting residue. The solution was stirred at 50° C. for 2 hours. Insoluble substance was filtered off and the filtrate was acidified with concentrated hydrochloric acid. The precipitated crystals were collected by filtration and recrystallized from methanol/water to give 6.8 g of phenylcarbamoylglycine.

3.9 g of phenylcarbamoylglycine was suspended in 50 ml of tetrahydrofuran. Under cooling, 2.0 ml of oxalyl chloride in small portions was added with stirring. After stirring for 3 hours at room temperature, tetrahydrofuran was distilled away under reduced pressure. The residue was dissolved in ethyl acetate, washed with water and brine, and dried over anhydrous sodium sulfate. Ethyl acetate was distilled away and the resulting residue was recrystallized from ethyl acetate/hexane to give 4.4 g of 3-carboxymethyl-1-phenylparabanic acid (Compound 59).

m.p.: 202°-203° C.

Elementary Analysis: $C_{11}H_8N_2O_5$

|  | C % | H % | N % |
|---|---|---|---|
| Calculated | 53.23 | 3.25 | 11.29 |
| Found | 53.32 | 3.07 | 11.11 |

MS (EI, 70 eV): 248 (M+), 119, 91, 64, 56.

IR (KBr): 3000-2500, 1780, 1730, 1720, 1430, 1255, 1140.

NMR(DMSO-$d_6$/TMS): $\delta = 4.38(s,2H)$, 7.42-7.57(m,4H), 13.44(bs,1H).

EXAMPLE 4

5.9 g of hydantoic acid was suspended in 100 ml of tetrahydrofuran, under cooling 5.1 ml of oxalyl chloride in small portions added with stirring. After stirring for 3 hours at room temperature, tetrahydrofuran was distilled away under reduced pressure. The residue was dissolved in ethyl acetate, washed with water and brine, and dried over anhydrous sodium sulfate. The solution was concentrated to dryness under reduced pressure and the resulting residue was recrystallized from ethyl acetate/hexane to give 3.1 g of 1-carboxymethylparabanic acid (Compound 60).

m.p.: 155°-158° C.

Elementary Analysis: $C_5H_4N_2O_5$

|  | C % | H % | N % |
|---|---|---|---|
| Calculated | 34.90 | 2.34 | 16.28 |
| Found | 34.78 | 2.09 | 16.13 |

MS (EI, 70 eV): 172 (M+), 127, 128, 100, 70, 56.

IR (KBr): 3000-2500, 1740, 1710, 1440, 1260, 1120.

NMR(DMSO-$d_6$/TMS): $\delta = 4.23(s,2H)$, 12.41(bs,1H), 13.36(bs,1H).

The following descriptions serve to illustrative pharmaceutical studies of the compounds of the present (1) Acute toxicity test The test compounds of the present invention were orally administered to groups of 8 Wistar-strain male rats, and the $LD_{50}$ values were calculated based on the death rate of 7 days. An example of the results is shown in Table 1.

TABLE 1

| Test compound | $LD_{50}$ (mg/kg) |
|---|---|
| Compound 44 | >5,000 |
| Compound 47 | >2,000 |
| Compound 48 | >5,000 |

(2) Aldose reductase inhibitory activity

Aldose reductase inhibitory activity of the compound of the present invention was evaluated by using aldose reductase prepared from rat lenses. The test compound was added to the reaction mixture consisting of phosphate buffer, NADPH and aldose reductase. After stability of absorbance was confirmed for a few minutes, glyceraldehyde was added to the reaction mixture and then the decrease in absorbance at 340 nm with the passage of time was measured to assay the inhibitory activity of the test compound against aldose reductase.

An example of the results is shown in Table 2. The inhibitory rate (%) against aldose reductase in the table is the values at $5\times 10^{-7}$M of the each test compound.

TABLE 2

| Test compound | Inhibitory rate (%) | Test compound | Inhibitory rate (%) |
|---|---|---|---|
| Compound 19 | 31 | Compound 47 | 75 |
| Compound 33 | 35 | Compound 48 | 75 |
| Compound 34 | 49 | Compound 49 | 30 |
| Compound 36 | 41 | Compound 50 | 42 |
| Compound 37 | 30 | Compound 51 | 42 |
| Compound 39 | 44 | Compound 52 | 37 |
| Compound 41 | 32 | Compound 53 | 47 |
| Compound 42 | 31 | Compound 54 | 57 |
| Compound 43 | 56 | Compound 55 | 36 |
| Compound 44 | 65 | Compound 57 | 25 |
| Compound 46 | 61 | Compound 60 | 31 |

As shown by the above mentioned results, the parabanic acid derivatives of the present invention have an excellent aldose reductase inhibitory activity as well as low toxicity. Therefore, the compounds are very useful as drugs for treatment and prevention of diabetic complications, for example, diabetic neuropathy, diabetic cataract and diabetic microangiopathy such as diabetic retinopathy, diabetic nephropathy or diabetic dermopathy, which are caused by excessive accumulation of intracellular sorbitol. Since the compounds of the invention have low toxicity and great safety, its long-term continuous administration and oral use are possible, so that they can be advantageously used especially in the treatment of chronic diseases.

The compounds of the present invention can be made into pharmaceutical compositions by combination with appropriate medicinal carriers or diluents, and can be formulated into preparations in solid, semisolid, liquid or gaseous form such as tablets, capsules, powders, granules, ointments, solutions, suppositories, injections, inhalants, aerosols and cataplasms in usual ways for oral or parenteral administrations.

In pharmaceutical dosage forms, the compounds of the present invention can be used in the form of their pharmaceutically acceptable salts, and also can be used alone or in appropriate association, as well as in combination with other pharmaceutically active components.

In case of oral preparations, the compounds can be used alone or combined with appropriate additives to make tablets, powders, granules or capsules, e.g. with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; with lubricants such as talc or magnesium stearate; and if desired, with diluents, buffering agents, moistening agents, preservatives and flavoring agents.

The compounds of the invention can be made into a suppository by mixing with a variety of bases, e.g. fatty and oily base such as cacao butter, emulsifying base or water-soluble base such as macrogol.

The compounds of the present invention can be formulated into a preparations for injections by dissolving, suspending or emulsifying in aqueous or non-aqueous solvent, such as distilled water for injection, physiologically saline solution, vegetable oil, synthetic aliphatic acid glycerides, esters of higher aliphatic acid or propylene glycol.

In case of inhalations or aerosol preparations, the compounds of the invention in the form of a liquid or minute powder can be filled up in an aerosol container with gas or liquid spraying agent, and if desired, with conventional adjuvants such as humidifying agents or dispersing agent. They can also be used as pharmaceuticals for a non-pressurized preparation such as in a nebulizer or an atomizer.

In order to make the compounds of the present invention into collyriums, they can be prepared as a solution or suspension together with an aqueous solvent such as sterile, purified water and physiologically saline solution, or a non-aqueous solvent for injection, if desired, with preservations, sterilizers, etc.

Furthermore, according to a kind of disease, the compounds of the invention can be formulated into other preparations suitable for treatment of the disease, such as ointment and cataplasms.

The desirable dose of the compounds of the present invention varies with the subject, form of the drug, method and period of administration. However, in order to obtain desirable effects, generally it is recommended to administer orally 10 to 4000 mg, preferably 20 to 2000 mg daily.

In case of parenteral administrations e.g. injections, doses of the compounds in the order of one tenth to one third of the above dose are preferable as daily doses.

Some prescriptions of the pharmaceutical compositions are shown below as examples which contain the compounds of the present invention as active ingredients.

| Prescription example 1 (tablet) | |
|---|---|
| Component | Content in a tablet (mg) |
| compound of this invention | 100 |
| lactose | 130 |
| corn starch | 40 |
| magnesium stearate | 10 |
| Total | 280 mg |

| Prescription example 2 (capsule) | |
|---|---|
| Component | Content in a capsule (mg) |
| compound of this invention | 50 |
| lactose | 250 |
| Total | 300 mg |

| Prescription example 3 (injection) | |
|---|---|
| Component | Content in an ampule (mg) |
| compound of this invention | 10 |
| sodium chloride | proper amount |

| distilled water for injection | proper amount |
|---|---|
| Total | 1 ml |

What is claimed is:

1. A compound of the formula:

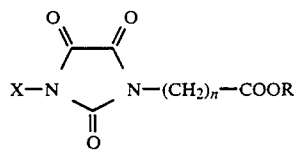

wherein R is hydrogen or a lower alkyl group, X is hydrogen, an alkyl group, a cycloalkyl group, a lower alkylcycloalkyl group, a phenyl group or a phenalkyl group which may be substituted by a lower alkyl group, a lower alkoxy group, a nitro group or a halogen, and n represents an integer of 1 to 4; or a pharmaceutically acceptable salt thereof.

2. A compound according to claim 1, wherein R is hydrogen.

3. A compound according to claim 2, wherein n is 1.

4. A compound according to claim 3, wherein X is a lower alkyl group.

5. A compound according to claim 3, wherein X is a phenalkyl group which may be substituted by a lower alkyl group a lower alkoxy group, a nitro group or a halogen.

6. A compound according to claim 5, wherein X is a phenalkyl group substituted by a lower alkyl group.

7. A compound according to claim 5, wherein X is a phenalkyl group substituted by a lower alkoxy group.

8. A compound according to claim 6, wherein X is a benzyl group.

9. A compound according to claim 6, wherein X is a phenethyl group.

10. A compound according to claim 5, wherein X is a phenalkyl group substituted by a nitro group.

11. A compound according to claim 5, wherein X is a phenalkyl group substituted by a halogen.

12. A pharmaceutical composition for use in treating diabetic complications comprising as an active ingredient an effective amount of a compound according to claim 1, or a pharmaceutically acceptable salt thereof, and a pharmaceutically acceptable carrier.

13. A method for treating diabetic complications which comprises administering to a subject in need of such treatment, an effective amount of a compound according to claim 1, or a pharmaceutically acceptable salt thereof.

* * * * *